: US 6,643,539 B2
(45) Date of Patent: Nov. 4, 2003

(12) United States Patent
Meij et al.

(54) ELECTROCARDIOGRAM SYSTEM FOR SYNTHESIZING LEADS AND PROVIDING AN ACCURACY MEASURE

(75) Inventors: Simon H. Meij, Mijnsheerenland (NL); Stefan P. Nelwan, Rotterdam (NL)

(73) Assignee: Siemens Medical Solutions USA, Inc., Malvern, PA (US)

( * ) Notice: Subject to any disclaimer, the term of this patent is extended or adjusted under 35 U.S.C. 154(b) by 261 days.

(21) Appl. No.: 09/844,443

(22) Filed: Apr. 27, 2001

(65) Prior Publication Data

US 2002/0035333 A1 Mar. 21, 2002

Related U.S. Application Data

(60) Provisional application No. 60/222,805, filed on Aug. 3, 2000.

(51) Int. Cl.$^7$ .............................................. A61B 5/0402
(52) U.S. Cl. ........................................ 600/509; 600/521
(58) Field of Search ................................. 607/509, 512, 607/521

(56) References Cited

U.S. PATENT DOCUMENTS

| 4,630,204 | A | * | 12/1986 | Mortara | 600/516 |
|---|---|---|---|---|---|
| 4,850,370 | A | * | 7/1989 | Dower | 600/512 |
| 5,058,598 | A | * | 10/1991 | Nicklas et al. | 600/512 |
| 5,318,037 | A | | 6/1994 | Evans et al. | 128/696 |
| 5,377,687 | A | | 1/1995 | Evans et al. | 128/700 |
| 5,711,304 | A | * | 1/1998 | Dower | 600/523 |
| 6,119,035 | A | * | 9/2000 | Wang | 600/509 |
| 6,217,525 | B1 | | 4/2001 | Medema et al. | 600/508 |
| 2002/0045837 | A1 | | 4/2002 | Wei et al. | 600/509 |
| 2002/0087088 | A1 | | 7/2002 | Brodnick | 600/509 |

FOREIGN PATENT DOCUMENTS

EP  1 221 299 A 2  7/2002

OTHER PUBLICATIONS

U.S. patent application Ser. No. 10/354,645, Tabbara et al., filed Jan. 30, 2003.
U.S. patent application Ser. No. 10/286,020, Tabbara et al., filed Nov. 1, 2002.
U.S. patent application Ser. No. 09/922,170, Meij et al., filed Mar. 3, 2001.

* cited by examiner

Primary Examiner—Jeffrey R. Jastrzab
(74) Attorney, Agent, or Firm—Alexander J. Burke

(57) ABSTRACT

An electrocardiogram (ECG) system provides a set of ECG lead signals. The system includes a source of a subset of ECG lead signals. A synthesizer, coupled to the ECG lead signal source, generates a set of synthesized ECG lead signals from the subset of ECG lead signals. Data is also generated representing the accuracy of the set of synthesized ECG lead signals.

23 Claims, 3 Drawing Sheets a)

| S | | M[V1] | | | | | | | | I |
|---|---|---|---|---|---|---|---|---|---|---|
| SI | = | 1 | 0 | 0 | 0 | 0 | 0 | 0 | 0 | I |
| SII | | 0 | 1 | 0 | 0 | 0 | 0 | 0 | 0 | II |
| SV1 | | CI(V1) | CII(V1) | 0 | CV2(V1) | CV3(V1) | CV4(V1) | CV5(V1) | CV6(V1) | V1 |
| SV2 | | 0 | 0 | 0 | 1 | 0 | 0 | 0 | 0 | V2 |
| SV3 | | 0 | 0 | 0 | 0 | 1 | 0 | 0 | 0 | V3 |
| SV4 | | 0 | 0 | 0 | 0 | 0 | 1 | 0 | 0 | V4 |
| SV5 | | 0 | 0 | 0 | 0 | 0 | 0 | 1 | 0 | V5 |
| SV6 | | 0 | 0 | 0 | 0 | 0 | 0 | 0 | 1 | V6 | b)

| S | | M[V1,V3] | | | | | | | | I |
|---|---|---|---|---|---|---|---|---|---|---|
| SI | = | 1 | 0 | 0 | 0 | 0 | 0 | 0 | 0 | I |
| SII | | 0 | 1 | 0 | 0 | 0 | 0 | 0 | 0 | II |
| SV1 | | CI(V1) | CII(V1) | 0 | CV2(V1) | 0 | CV4(V1) | CV5(V1) | CV6(V1) | V1 |
| SV2 | | 0 | 0 | 0 | 1 | 0 | 0 | 0 | 0 | V2 |
| SV3 | | CI(V3) | CII(V3) | 0 | CV2(V3) | 0 | CV4(V3) | CV5(V3) | CV6(V3) | V3 |
| SV4 | | 0 | 0 | 0 | 0 | 0 | 1 | 0 | 0 | V4 |
| SV5 | | 0 | 0 | 0 | 0 | 0 | 0 | 1 | 0 | V5 |
| SV6 | | 0 | 0 | 0 | 0 | 0 | 0 | 0 | 1 | V6 |

Fig. 3

ELECTROCARDIOGRAM SYSTEM FOR SYNTHESIZING LEADS AND PROVIDING AN ACCURACY MEASURE

This application is a non-provisional application based on the provisional application serial No. 60/222,805, filed Aug. 3, 2000 and titled "Signal Processing Apparatus, Monitoring Method, User Inteface, and Analysis System for Synthesizing an Electrocardiogram.

FIELD OF THE INVENTION

The present invention relates to electrocardiogram (ECG) systems, and in particular to ECG systems which can provide synthesized signals corresponding to signals generated from electrodes which provide the actual ECG signals.

BACKGROUND OF THE INVENTION

ECG systems are well known, and provide information about the physiological status of a patient's heart to a physician. More specifically, so called 12 lead ECG systems exist which provide twelve waveforms, called leads, to the physician. To provide such a 12 lead ECG, ten electrodes are placed on the patient's body, and the signals from these electrodes are processed to provide the twelve leads, all in a known manner. These ten electrodes include four electrodes which provide signals processed to generate six of what are known as limb leads, and six electrodes which provide signals processed to provide six of what are known as precordial or chest leads.

However, such a system does not always operate in the ideal manner. Sometimes, electrodes slip on, or work loose from, a patient's body and produce a null signal, or produce signals which are otherwise degraded to the point of being unusable. Furthermore, the location on the patient's body at which one or more of the electrodes should be placed may be unavailable due to injury or surgery. In addition, under some circumstances it may be desirable to place an electrode at a location on the body different from the normally used locations. It is desirable under these conditions to still provide the signals needed to generate the 12 lead ECG.

It is known that the signals representing the respective lead signals contain mutually redundant information. It is also known that, should one electrode be missing or malfunctioning, an appropriate combination of signals from the other electrodes and/or the other leads, which are available and functional, can be used to generate a synthesized signal which closely approximates the lead signal derived from the missing or malfunctioning electrode. To apply this technique, at least some portion of a full 12 lead ECG is recorded, during an analysis phase. The recorded signals are then processed to generate a function, which may be applied to the lead signals which are available, to synthesize a lead signal which approximates the lead signal which is missing or distorted beyond use. During a synthesis phase, this function is then applied to the available ECG lead signals. Using this technique, a missing lead may be synthesized.

In U.S. Pat. No. 5,058,598, issued Oct. 22, 1991 to Nicklas et al., a system is disclosed for synthesizing a desired precordial lead from what is termed a set of base leads. First, in an analysis phase, a set of ECG lead signals, including at least the set of base leads (in Nicklas et al, the base leads are leads I, II, and V2), and the precordial lead signal (other than V2) which is desired to be synthesized, is processed to generate coefficients for a linear equation. Then, in a synthesis phase, signals representing only the base leads are received, and the values of those base leads are substituted into the linear equation to derive values which represent the desired synthesized precordial lead signal. Nicklas et al. also discloses partitioning the ECG complex into segments (e.g. QRS, ST, etc.), and processing each segment separately to generate respective sets of coefficients for a separate linear equation corresponding to each segment. In this case, during the synthesis phase, values for each segment from the base leads are substituted into the appropriate linear equation, to derive values which represent the desired synthesized precordial lead signal in that segment.

In U.S. Pat. No. 5,490,515, issued Feb. 13, 1996 to Mortara, a system is disclosed for synthesizing a single specified lead from a set of eight lead signals. In the analysis phase, the set of eight lead signals, derived from respective electrodes, is received by the system and a coefficient table, having entries representing coefficients of a set of linear equations, is generated. In the synthesis phase, the coefficient table is then used to synthesize a selected one of the eight lead signals, based on the values of the other seven lead signals. Mortara also discloses simultaneously synthesizing more than one missing lead.

In neither of these systems is any indication of the accuracy of the synthesized signal provided to the operator. In addition, in neither of these systems is any information provided to the operator to assist in preparation for the ECG, nor in interpreting the displayed 12 ECG lead waveforms.

It is desirable to determine the accuracy of the synthesized signal relative to other potential synthesized signals, and to provide that information to the operator. It is further desirable to provide information to the operator to assist in the preparation for the ECG and the interpretation of the results. In some cases, such as telemetered ECGs, it is further desirable to monitor patients with a minimum number of electrodes, while producing a full 12 lead ECG and maintaining a desired level of accuracy.

BRIEF SUMMARY OF THE INVENTION

In accordance with principles of the present invention, an electrocardiogram (ECG) system provides a set of ECG lead signals. The system includes a source of a subset of ECG lead signals. A synthesizer, coupled to the ECG lead signal source, generates a set of synthesized ECG lead signals from the subset of ECG lead signals. Data is also generated representing the accuracy of the set of synthesized ECG lead signals.

BRIEF DESCRIPTION OF THE DRAWING

In the drawing:

FIG. 3 is a diagram illustrating matrix calculations which are useful in understanding the operation of the present invention.

DETAILED DESCRIPTION OF THE INVENTION

Figure 1:
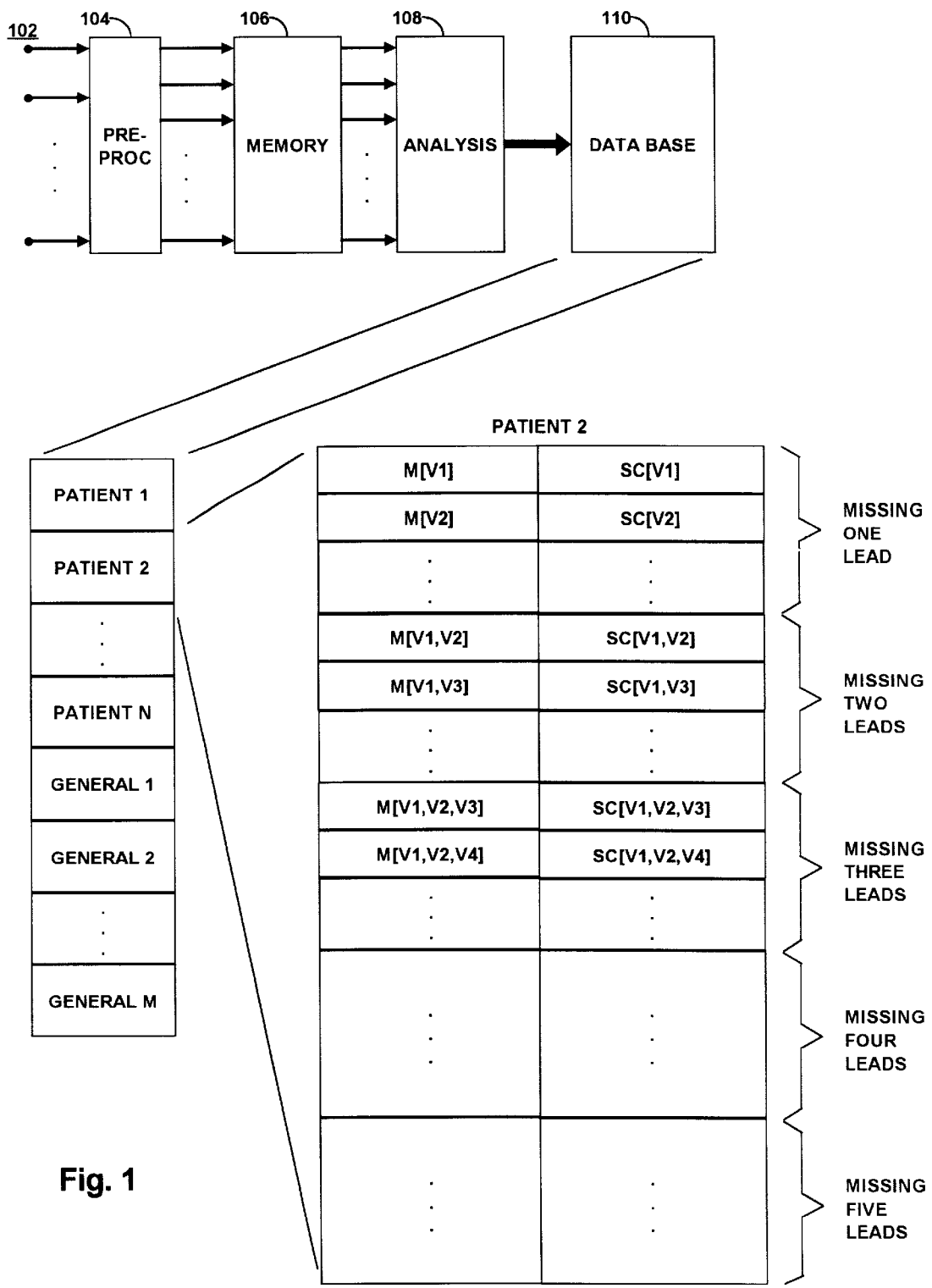
FIG. 1 is a diagram in block form with the database block also shown in memory layout form, illustrating a portion of an ECG system according to principles of the present invention.

FIG. 1 is a diagram in block form with the database block also shown in memory layout form, illustrating a portion of an ECG system according to principles of the present invention. In FIG. 1, a plurality 102 of electrodes are intended to be attached to respective locations on a patient's body. The plurality 102 of electrodes are coupled to respective input terminals of a preprocessor 104. Respective output terminals of the preprocessor 104 are coupled to corresponding input terminals of a memory 106. Respective output terminals of the memory 106 are coupled to corresponding input terminals of an analysis circuit 108. An output terminal of the analysis circuit 108 is coupled to an input terminal of a database 110.

In operation, the plurality 102 of electrodes are ECG electrodes which are intended to be attached to predetermined locations on a patient. In the illustrated embodiment, 10 electrodes are provided. The preprocessor 104 processes the signals from the 10 electrodes to generate signals representing a 12 lead ECG at respective output terminals. More specifically, signals from the four limb lead electrodes are processed to provide limb lead signals I and II. From limb lead signals I and II, the remaining limb lead signals III, aVR, aVL and aVF, may be mathematically derived. In the illustrated embodiment, the derivation of those other limb lead signals is not germane to the present invention and they are not discussed in the remainder of this application. The other six electrodes are processed separately to provide corresponding precordial lead signals (V1, V2, V3, V4, V5, V6). Thus, signals representing eight lead signals (I, II, V1, V2, V3, V4, V5, V6) are generated by the preprocessor 104 in a known manner and are further processed in the manner described below.

In the illustrated embodiment this preprocessing further includes analog-to-digital conversion. The eight lead signals, therefore, are in multibit digital form. The preprocessor 104 may further provide processing to identify characteristics of each ECG complex and to time align and aggregate (e.g. average, median filter, etc.) some number of successive ECG complexes for each lead, all in a known manner. Digital data representing the eight, possibly averaged, ECG lead complexes is stored, in a known manner, in respective locations in the memory 106.

Figure 2:
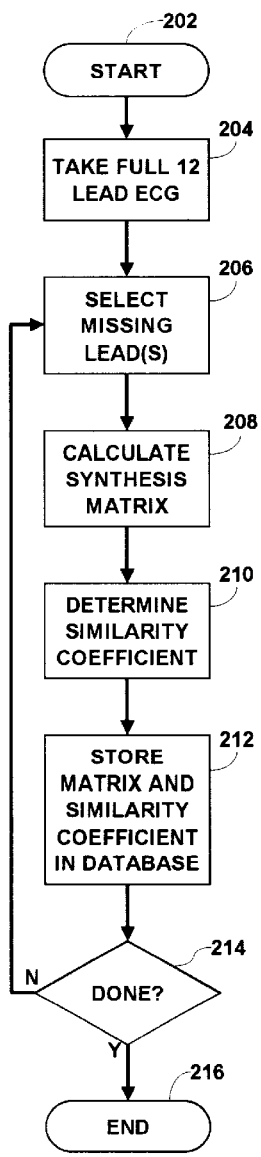
FIG. 2 is a flowchart useful in understanding the operation of the system illustrated in FIG. 1.

FIG. 2 is a flowchart useful in understanding the analysis phase operation of the analysis system illustrated in FIG. 1. The operation starts in block 202. In block 204 a full 12 lead ECG is taken and the result, as described above, is multibit digital data representing eight respective ECG lead complexes (I, II, V1, V2, V3, V4, V5, V6), possibly aggregated. The data representing these eight lead complexes are stored in respective locations in the memory 106, all in a known manner.

The analysis circuit 108 retrieves data, in a known manner, from the locations in the memory 106 corresponding to the eight lead complexes. The analysis circuit 108 then analyzes the retrieved data. In general, every possible combination of one or more of the leads is treated as if it were missing or otherwise unusable. Then, for each such combination, the other remaining lead complexes, treated as if they remain available, are compared to the missing lead complex or complexes, and a function of the available lead complexes is calculated which will most accurately synthesize the one or more missing leads from the available leads. A measure of the accuracy of the synthesis is also determined and both the calculated function and the determined accuracy measure are stored in the database 110. The processing applied to each such combination is illustrated in FIG. 2 and described in more detail below.

In block 206 a subset of leads, consisting in the first place of one of the eight leads, is selected as the missing lead. For the purposes of the following description, the selected lead is the precordial lead V1. In block 208, the stored lead complex data representing the selected lead V1 is compared to the stored lead data representing the other seven lead complexes (I, II, V2, V3, V4, V5 and V6) to calculate a function of those other seven lead complexes (I, II, V2, V3, V4, V5 and V6) which will most closely approximate the selected lead complex (V1).

In the illustrated embodiment, a lead complex SV1, approximating the selected lead complex V1, is synthesized by a linear combination of the other seven lead complexes (I, II, V2, V3, V4, V5 and V6). That synthesis is represented by a set of coefficients {CI(V1), CII(V1), CV2(V1), CV3(V1), CV4(V1), CV5(V1) and CV6(V1)}. The notation Cx(y) is intended to represent the coefficient C to be applied to the $x^{th}$ available lead complex to synthesize the missing $y^{th}$ lead complex. That is, this set of coefficients represents the proportion of the other seven lead complexes (I, II, V2, V3, V4, V5 and V6), respectively, in the linear combination representing the synthesized lead complex SV1 most closely approximating the missing lead complex V1. In the illustrated embodiment, the coefficients are calculated using a least squares linear regression with a zero intercept vector, in a known manner. One skilled in the art will understand that any form of combination, such as polynomial or trigonometric, could also be used.

The calculation in block 208 produces a synthesis matrix M. FIG. 3 is a diagram illustrating matrix calculations which are useful in understanding the operation of the present invention. In FIG. 3a, a matrix M[V1] illustrates a matrix which is produced when the selected lead is lead V1. The notation M[z] is intended to represent the synthesis matrix M for synthesizing the synthesized vector S from an input vector I missing the set {z} of ECG lead complexes. An input vector I contains elements representing data points from the eight lead complexes (I, II, V1, V2, V3, V4, V5, V6). The matrix M[V1] has as its basis an identity matrix. However, the row corresponding to the synthesized lead complex SV1 (e.g. the third row from the top) is replaced by the set of coefficients {CI(V1), CII(V1), 0, CV2(V1), CV3 (V1), CV4(V1), CV5(V1) and CV6(V1)} calculated in block 208 by the analysis circuit 108. The column corresponding to the selected lead complex V1 (e.g. the third column from the left) is set to zero, so that the selected lead complex V1 makes no contribution to the combination forming the synthesized selected lead complex SV1.

One skilled in the art will understand that when the synthesis matrix M[V1] is multiplied by the input vector I, the result is a synthesized vector S. The synthesized vector S contains elements representing synthesized data points for the eight synthesized lead complexes (SI, SII, SV1, SV2, SV3, SV4, SV5, SV6), in which the synthesized lead complex SV1 for the selected lead is synthesized from the other seven leads (I, II, V2, V3, V4, V5, V6) while the remaining leads (SI, SII, SV2, SV3, SV4, SV5, SV6) are equal to the corresponding elements in the input vector I.

In block 210 a similarity coefficient SC is determined in the following manner. When the matrix M[V1] has been calculated in block 208, it is used to generate eight synthesized lead complexes (SI, SII, SV1, SV2, SV3, SV4, SV5, SV6). Then the synthesized lead complexes (SI, SII, SV1, SV2, SV3, SV4, SV5, SV6) are compared to the actual leads complexes (I, II, V1, V2, V3, V4, V5, V6) stored in the memory 106 to calculate a similarity coefficient SC. This is designated in FIG. 2 as SC(V1) to indicate that it is the similarity coefficient SC for the selected lead V1. In the illustrated embodiment, this coefficient SC[V1] is calculated from the differences between the root mean square (RMS) values of the synthesized lead complex data (SI, SII, SV1, SV2, SV3, SV4, SV5, SV6) and the stored actual lead complex data (I, II, V1, V2, V3, V4, V5, V6). More specifically, the synthesis coefficient is calculated as $$SC = 1 - \frac{RMS_{source} - RMS_{error}}{RMS_{source}}.$$

Alternatively, the known Pearson's correlation technique may be used to generate a similarity coefficient SC. One skilled in the art will understand, however, that any technique of rating the similarity of the synthesized lead complexes to the actual lead complexes may be used.

In step 212, the calculated matrix M[V1] and the corresponding similarity coefficient SC[V1] are stored in the database 110 in a known manner. The database 110 is maintained on a non-volatile storage device. For example, the database may be located on a disk drive system in a central location accessible by a hospital network, in a known manner. The specific configuration of the storage device and database 110 is not germane to the invention, provided it is accessible by the ECG system.

One skilled in the art will understand from FIG. 1 that the database 110 contains a plurality of entries respectively corresponding to different patients and to different general populations. This will be described in more detail below. Each patient and general population entry contains a sequence of synthesis entries corresponding to different sets of selected (missing) lead complexes, derived as described above. In FIG. 1, the entry for patient 2 is illustrated. The patient 2 entry in turn contains a first synthesis entry into which the matrix M[V1] and the similarity coefficient SC[V1] is stored. Other data not germane to the present invention may also be stored in the patient entry and/or the patient entry's synthesis entries.

In block 214, if all the synthesis entries have been filled, then the process ends in block 216. Otherwise processing returns to block 206 where another subset of leads is selected and treated as missing. In the illustrated embodiment, all subsets consisting of a single missing lead are processed, followed by all subsets consisting of two missing leads, all subsets consisting of three missing leads, and so forth. One skilled in the art will understand that the order in which the subsets are determined and processed is not germane to the present invention.

More specifically, in the illustrated embodiment, the precordial lead V2 is selected next and the processing described above performed again. In this case, referring again to FIG. 1, the results of this processing, M[V2] and SC[V2], are stored in the second synthesis entry in the patient 2 entry. This continues for all of the remaining subsets of a single missing lead. Then all sets of two simultaneously missing leads are processed. For example, leads V1 and V2 are simultaneously selected and treated as missing and the same processing described above performed and the results, synthesis matrix M[V1,V2] and similarity coefficient SC[V1, V2], are stored in the appropriate patient 2 synthesis entry. Then the next set of two missing leads, V1 and V3 are simultaneously selected and treated as missing and the same processing performed.

FIG. 3b illustrates a matrix M[V1,V3] which is calculated in response to the simultaneous selection of leads V1 and V3 as missing. As before, the matrix M[V1,V3] has as its basis the identity matrix. But in this case the row corresponding to the synthesized lead SV1 is replaced with coefficients CI(V1), CII(V1), 0, CV2(V1), 0, CV4(V1) CV5(V1) and CV6(V1) and the row corresponding to the synthesized lead SV3 is replaced with coefficients CI(V3), CII(V3), 0, CV2 (V3), 0, CV4(V3), CV5(V3) and CV6(V3). At the same time, the columns corresponding to the selected lead complexes V1 and V3 are replaced with zeroes to ensure that input signals from those lead complexes do not contribute to the synthesized lead signals. Again, a similarity coefficient SC[V1,V3] is determined and both the matrix M[V1, V3] and the similarity coefficient SC[V1,V3] are stored in the appropriate synthesis entry in the patient 2 entry. This continues for all sets of two missing leads, followed by all combinations of three missing leads and so forth until the patient 2 entry is completed and the process ends in block 216 (of FIG. 2).

As was disclosed in Nicklas et al. it is possible to partition each of the eight lead complexes stored in the memory 108 into segments, and perform the calculations described above on each segment independently. In the present invention, this would result in a plurality of matrices, one for each segment, stored in each synthesis entry in the patient 2 entry. When the missing lead(s) is synthesized from the available leads, the appropriate matrix is used depending on which segment is currently being synthesized, all as disclosed in Nicklas et al.

Figure 4:
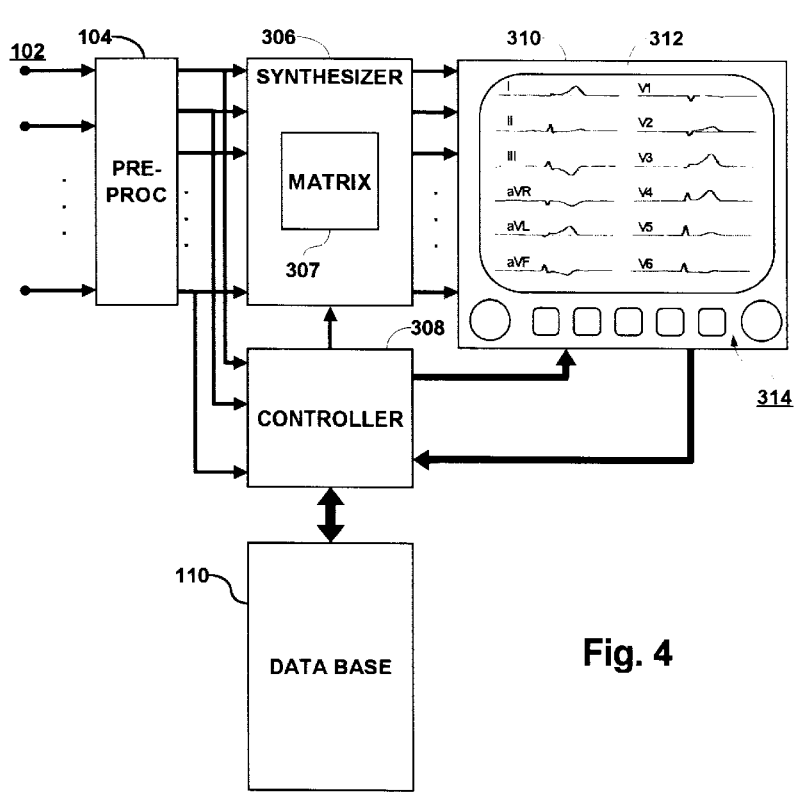
FIG. 4 is a block diagram illustrating a different portion of a system according to principles of the present invention.

FIG. 4 is a block diagram illustrating a synthesis portion of a system according to principles of the present invention. In FIG. 4, those elements which are the same as those illustrated in FIG. 1 are designated by the same reference number and are not described in detail below. In FIG. 4, the respective output terminals of the preprocessor 104 are coupled to corresponding input terminals of a synthesizer 306 and a controller 308. Respective output terminals of the synthesizer 306 are coupled to corresponding data input terminals of a display device 310. A synthesizer control output terminal of the controller 308 is coupled to a control input terminal of the synthesizer 306, and a display device control output terminal of the controller 308 is coupled to a control input terminal of the display device 310. The display device includes a display screen 312 and a set of user controls 314. These user controls 314 may include, among other controls, knobs, illustrated as circles, and buttons, illustrated as rounded squares. A user control output terminal of the display device 310 is coupled to a user control input terminal of the controller 308. A bidirectional terminal of the controller 308 is coupled to a corresponding terminal of the database 110.

As illustrated in FIG. 4, the display device 310 can display the 12 lead ECG waveforms from the synthesizer 306 on the display screen 312 in the usual manner for ECG waveforms. In addition, the controller 308 can respond to user input from the user controls 314 on the display device 310, and can condition the display device 310 to display information on the display screen 312. The controller 308 can also control the operation of the synthesizer 306 in response to the lead signals from the preprocessor 104, in a manner to be described in detail below. The synthesizer 306 in turn performs the matrix multiplication illustrated in FIG. 3 on the lead signals received from the preprocessor 104 to generate the lead signals, possibly including synthesized lead signals, for the display device 310.

In general operation, the plurality of electrodes 102 are attached to predetermined locations on a patient by an operator. The operator then manipulates the user controls 314 to enter information concerning the monitoring desired, including, e.g. the identification of the patient. The controller 308 then conditions the synthesizer 306 to operate in a normal mode. The preprocessor 104 provides the eight lead signals to the synthesizer 306. In the normal mode, all of the plurality 102 of electrodes are operational, and all lead signals from the preprocessor 104 are accurate. The controller 308 conditions the synthesizer 306 to pass the input lead signals through to the output without change. This may be done by placing an identity matrix in the matrix 307 of the synthesizer 306. The synthesizer 306 performs the matrix multiplication illustrated in FIG. 3 using the identity matrix to transfer the received 12 lead signals to the display device 310. The display device 310, in turn, displays the 12 lead ECG waveforms from the synthesizer 306 on the display screen 312 all in a normal manner. In this mode of operation, the similarity coefficient has its maximum value.

As described above, however, it is possible for one or more electrodes to detach from the patient. This may be detected automatically by the controller 308 by any of a number of known techniques. For example, if no pulse component is detected in a lead signal, then that lead signal may be identified as inoperative. In this case, the controller 308 retrieves the entry from the database 110 for the current patient, e.g. patient 2 (of FIG. 1), and from that entry retrieves the matrix M appropriate for synthesizing the lead or leads which have been identified as inoperative. The controller 308 then inserts that matrix M into the matrix 307 in the synthesizer 306. The synthesizer 306 performs the matrix multiplication described above with reference to FIG. 3, to provide a synthesized signal for the lead or leads which are inoperative. The display device 310 continues to display the 12 lead waveforms received from the synthesizer 306, including the synthesized lead waveform or waveforms.

The controller 308 may further condition the display device 310 to display an indication on the display screen 312 to alert the operator that one or more of the displayed leads are being synthesized. This indication may include highlighting the synthesized lead waveform(s), or the background of the synthesized lead waveform(s), in some fashion, such as varying the intensity or color of the synthesized lead waveform(s) relative to the other lead waveforms; or placing an indicative symbol in the vicinity of the synthesized waveform(s); or displaying a textual identification of the synthesized waveform(s) on the display screen 312. In addition, the controller 308 may retrieve the corresponding similarity coefficient SC from the database 110 and display that on the display screen 312 as an indication of the expected accuracy of the displayed waveforms.

Also as described above, all the desired locations on the body of the patient may not be available due to surgery or injury. In this case, the operator can manipulate the user controls 314 to provide an indication of the sites which are unavailable to the controller 308. The controller 308 will then generate a list of electrode configurations for the available locations, and access the data in the database 110 entry associated with this patient to retrieve the similarity coefficients SC associated with each of the electrode configurations. The configuration with the highest similarity configuration SC, i.e. generating the most accurate 12 lead ECG waveform synthesis, is then displayed on the display screen 312 of the display device 310. The controller 308 retrieves the matrix M associated with that configuration and places it in the matrix 307 in the synthesizer 306. In accordance with the displayed information, the operator then applies the electrodes in this desired configuration. Then the display of the 12 lead ECG waveforms can proceed as described above, optionally including specially highlighting the synthesized lead waveforms and displaying the similarity coefficient.

Alternatively, the complete list of available electrode configurations along with their similarity coefficients may be displayed on the display screen 312 of the display device 310. The operator can then select one of the available configurations based not only on the similarity coefficients but possibly also on other clinical considerations. The operator then manipulates the user controls 314 to indicate which of the configurations has been selected, and applies the electrodes in that configuration. The controller 308 retrieves the appropriate matrix M from the database 110 and supplies it to the matrix 307 in the synthesizer 306. The controller 308 then conditions the synthesizer 306 to synthesize the 12 lead ECG waveforms for that configuration, as described above.

By either automatically specifying the electrode configuration with the highest similarity coefficient, or by providing a list of electrode configurations with an associated similarity coefficient to the operator for selection, it is assured that an electrode configuration producing 12 lead ECG waveforms with the maximum accuracy, or the maximum accuracy given the existing clinical considerations, will be displayed.

It is sometimes desired to use a non-standard electrode configuration. For example, a physician may desire data related to the right side of the heart, or further around the left side of the heart. The former requires one or more electrodes placed at locations to the right of the heart, and the latter at locations further to the left of the heart. There are predetermined such locations known as V1R, V2R, V3R, V4R, V5R and V6R on the right side of the chest and V7, V8 and V9 around the left side of the patient. Prior systems required either extra electrodes and circuitry to process signals and display the waveforms from them, or that electrode(s) be removed from the standard locations V1, V2, V3, V4, V5 and V6 to be placed at the other location(s) V7, V8, V9, V1R, V2R, V3R, V4R, V5R and V6R. Moving a lead from a standard location meant losing the lead signal generated by that electrode.

In the system illustrated in FIG. 4, the operator manipulates the user controls 314 on the display device 310 to indicate that it is desired to move one or more of the electrodes from their standard locations to another location. In response, the controller 308 retrieves the entry in the database 110 corresponding to the patient, and retrieves all of the similarity coefficients SC for the configurations missing the number of leads desired to be moved. That is, if two leads are desired to be moved, then the controller 308 retrieves the similarity coefficients SC for all of the configurations missing two leads. The controller 308 then automatically selects the configuration having the highest similarity coefficient SC from among those retrieved, and displays information on the display screen 312 of the display device 310 specifying the electrode configuration corresponding to that similarity coefficient SC. The operator places the appropriate electrodes at the specified locations on the patient, and then places the remaining leads at the other desired locations.

The controller 308 then retrieves the matrix M corresponding to the specified electrode configuration from the database 110 and supplies it to the matrix 307 in the synthesizer 308. The synthesizer 306 then synthesizes the standard 12 lead ECG waveforms from the available leads in the standard locations in the manner described above. The controller 308 may further condition the display device 310 to simultaneously display the 12 lead ECG waveforms and the lead waveforms from the other locations (e.g. from the right side of the chest) on the display screen 312, in a known manner. As before, the synthesized waveforms may be specially identified on the display screen and/or the similarity coefficient displayed.

As before, alternatively, a list of possible electrode configurations with their respective similarity coefficients, may be displayed on the display screen 312 of the display device 310, from which the operator selects one based on the similarity coefficients and other clinical considerations. The operator manipulates the user controls to select one of the configurations and the controller 308 conditions the system to operate in that configuration as described above. Again, as before, use of the similarity coefficients permits synthesis of the standard 12 lead ECG waveforms having the maximum accuracy, or the maximum accuracy based on existing clinical considerations.

In some situations, the use of the full set of 10 electrodes to produce the full 12 lead ECG is not desirable, for example, if a patient is being transported from one location to another, or if the ECG is being monitored by telemetry. In these situations, it is desired to use the minimum number of electrodes for patient comfort, while still maintaining a desired level of accuracy in the ECG.

Under these situations, the controller 308 retrieves the patient entry from the database 110. The similarity coefficients SC for all the synthesis entries corresponding to one missing lead are compared, and the entry with the largest similarity coefficient is selected. Similarly the similarity coefficients for all the synthesis entries corresponding to two missing leads are compared and the entry with the largest similarity coefficient is selected. This is repeated for each possible number (three, four, etc.) of missing leads. Then the list of selected entries, including the electrode configuration and the similarity coefficient, is displayed on the display screen 312 of the display device 310. The operator then selects the entry which satisfies the minimum accuracy desired using the user controls 314, and attaches the electrodes to the patient according to the configuration represented by that entry. The controller 308 conditions the system to synthesize the 12 lead ECG from the selected electrode configuration. In this manner, the highest accuracy for the number of electrodes selected is guaranteed, while minimizing to the extent possible the number of electrodes necessary, thus, minimizing patient discomfort.

In the preceding description, it was assumed that a full 12 lead ECG for the patient was previously available to be analyzed. This may not always be the case. In those cases, of course, there can be no entry in the database 110 for that patient. Referring again to FIG. 1, 12 lead ECG data from a large population may be analyzed by the analysis circuit 108 as a group, in the manner illustrated in FIG. 2. In this case, the eight lead complexes assembled in the memory 106 by block 204 will be generated as the aggregation of all the available eight lead ECG complexes for all the people in the population. These general-population lead complexes will be analyzed in the manner illustrated in FIG. 2 above to produce a set of general-population matrices M and corresponding similarity coefficients SC. This set of matrices M and similarity coefficients SC will be stored in a general population entry in the database 110, illustrated in FIG. 1 as an entry labeled GENERAL 1. The entry GENERAL 1 has exactly the same data structure as that illustrated for Patient 2. The data in the GENERAL 1 entry is based on the aggregated 12 lead complexes for the entire population, however.

If a patient does not have an entry in the database 110, then the general population entry GENERAL 1 is retrieved, and the data in that entry used in exactly the same manner as described above for any of the situations described above: e.g. synthesizing detached electrodes, or synthesizing leads for electrodes whose locations are unavailable or which have been purposely moved to another location. When sufficient complete 12 lead ECG complexes have been accumulated for the patient, then the analysis described above with reference to FIG. 1 and FIG. 2 is performed on those complexes, a new entry in the database 110 is created for the patient containing the matrices and associated similarity coefficients resulting from that analysis, and the processing continues as described above using the newly created entry in the database 110.

It is also possible to partition the people in the general population discussed above into groups termed categories. For example, groupings may be made by sex, by weight, by age group, by disease and/or by cardiac health (e.g. normal, ischemic/acute myocardial infarction, bundle branch blockage, etc.). The ECG complexes associated with the general population of patients may be partitioned in a corresponding manner and analyzed separately as described above with reference to FIG. 1 and FIG. 2 to produce further category-specific general-population entries in the database 110, designated as GENERAL 2 to GENERAL M in FIG. 1.

When a patient is being prepared for an ECG, the operator manipulates the user controls 314 on the display device 310 to supply characteristics of the patient (name, sex, age, weight, etc.) to the controller 308. As described above, the controller 308 queries the database 110 for a patient entry for that patient. If a patient does not have a patient entry in the database 110, then the other characteristics related to that patient are processed by the controller 308 to assign the patient to one of the available categories. The controller 308 then retrieves the category-specific general population entry corresponding to the category to which the patient was assigned, and uses the synthesis entries in that entry to provide a 12 lead ECG until that patient is assigned his own entry in the database 110.

What is claimed is:

1. An electrocardiogram (ECG) system, comprising:
    a source of a plurality of subsets of data representing ECG lead signals associated with a corresponding plurality of sets of ECG electrode configurations;
    a synthesizer, coupled to the ECG lead signal source, for generating a plurality of sets of data representing synthesized ECG lead signals from the plurality of subsets of data representing ECG lead signals;
    a source of data representing a plurality of accuracy values corresponding to the plurality of sets of data representing synthesized ECG lead signals; and
    a display generator for initiating generation of data representing at least one display image identifying a plurality of accuracy values and identifying the corresponding plurality of sets of ECG electrode configurations and enabling a user to select a configuration based on accuracy values.

2. The system of claim 1 wherein the display image identifies the plurality of sets of ECG electrode configurations enabling a user to select a configuration based on electrode positions.

3. The system of claim 1 wherein
    the synthesizer comprises circuitry for calculating a function of the subset of ECG lead signals to generate the set of synthesized ECG lead signals and further comprising
        an analyzer, coupled to the synthesizer and the accuracy representative data source, and responsive to a set of preexisting ECG lead signals, for generating the function of the subset of ECG lead signals and the accuracy representative data.

4. The system of claim 3 wherein the analyzer comprises circuitry, responsive to the set of preexisting ECG lead signals, for calculating respective coefficients of a linear equation representing the function and an individual coefficient is associated with an individual ECG lead signal in the subset of ECG lead signals.

5. The system of claim 1 wherein
said synthesizer adaptively generates a set of data representing a selected one of (a) patient specific synthesized ECG lead signals and (b) patient independent synthesized ECG lead signals, in response to user command.

6. The system of claim 1 wherein an accuracy value comprises a similarity coefficient.

7. The system of claim 6 wherein said accuracy value is responsive to the RMS values of the preexisting ECG lead signals and the synthesized ECG lead signals.

8. The system of claim 6 wherein said similarity coefficient SC comprises $$SC = 1 - \frac{RMS_{source} - RMS_{error}}{RMS_{source}}$$

where $RMS_{source}$ represents the RMS value of the preexisting ECG lead signals and $RMS_{error}$ represents the RMS value of the difference between the preexisting ECG lead signals and the synthesized ECG lead signals.

9. The system of claim 1 wherein said user is able to select a configuration based on at least one of, (a) accuracy values and (b) clinical considerations, by selecting an image element in said at least one display image.

10. The system of claim 1, wherein the ECG lead signal source comprises:
a set of electrodes; and
a preprocessor, responsive to respective signals from the electrodes to generate said plurality of subsets of data representing ECG lead signals associated with said corresponding plurality of sets of ECG electrode configurations.

11. The system of claim 1, wherein:
the ECG lead signal source generates an input vector representing an individual subset of ECG lead signals; and
the synthesizer comprises:
a matrix for containing a function of said individual subset of ECG lead signals; and
a processor for performing a matrix multiplication of the matrix times said input vector to generate a corresponding output vector comprising a subset of data representing ECG lead signals.

12. The system of claim 1, further comprising
a database, containing a plurality of functions respectively corresponding to said plurality of subsets of data representing ECG lead signals associated with a corresponding plurality of sets of ECG electrode configurations; and
a controller, coupled between the database and the synthesizer, and comprising:
circuitry for retrieving from the database the function corresponding to an individual subset of ECG lead signals; and
circuitry for conditioning the synthesizer to apply the retrieved function to said individual subset of ECG lead signals.

13. The system of claim 1, including,
a database containing a plurality of matrices respectively representing a plurality of functions;

a function retrieving processor for retrieving from the database the matrix corresponding to an individual subset of ECG lead signals;
a conditioning processor for supplying the retrieved matrix to the synthesizer; and wherein
the ECG lead signal source generates an input vector representing said individual subset of ECG lead signals; and the synthesizer,
receives the retrieved matrix corresponding to said individual subset of ECG lead signals; and
multiplies said input vector and retrieved matrix to generate a corresponding output vector representing ECG lead signals.

14. The system of claim 1 wherein:
said synthesizer adaptively generates a set of data representing a selected one of, (a) patient specific synthesized ECG lead signals and (b) patient independent synthesized ECG lead signals, together with an associated accuracy representative value, in response to user command.

15. The system of claim 14,
wherein said synthesizer adaptively generates a set of data representing ECG lead signals in at least one of, (i) standard electrode positions and (ii) non-standard electrode positions.

16. The system of claim 1 further comprising:
a memory, responsive to the set of preexisting ECG lead signals, for storing respective ECG complexes respectively corresponding to the ECG lead signals;
and a processor, coupled to the memory, for calculating a plurality of functions, and associated accuracy values, in response to the stored ECG complexes.

17. The system of claim 16 wherein said function comprises a matrix.

18. A method supporting operation of an electrocardiogram (ECG) system, comprising the steps of:
storing a plurality of subsets of data representing ECG lead signals associated with a corresponding plurality of sets of ECG electrode configurations;
generating a plurality of sets of data representing synthesized ECG lead signals from the plurality of subsets of data representing ECG lead signals;
storing data representing a plurality of determined accuracy values corresponding to the plurality of sets of data representing synthesized ECG lead signals; and
initiating generation of data representing at least one display image identifying a plurality of accuracy values and identifying the corresponding plurality of sets of ECG electrode configurations and enabling a user to select a configuration based on accuracy values.

19. An electrocardiogram (ECG) system, comprising:
a source of a plurality of subsets of data representing ECG lead signals associated with a corresponding plurality of sets of ECG electrode configurations;
a synthesizer, coupled to the ECG lead signal source, for employing the plurality of subsets of data representing ECG lead signals in adaptively generating a set of synthesized data representing a selected one of, (a) patient specific synthesized ECG lead signals and (b) patient independent synthesized ECG lead signals; and
a display generator for initiating generation of data representing at least one display image showing said synthesized data.

20. A system according to claim 19, wherein
said synthesizer automatically selects to perform said selected one of, (a) said patient specific ECG lead signal synthesis and (b) said patient independent ECG lead signal synthesis in response to a determination a subset of data representing patient specific ECG lead signals is available.

21. A system according to claim 19, wherein
said synthesizer adaptively generates said set of synthesized data in response to user selection, via said at least one display image, of synthesis of said selected one of, (a) patient specific synthesized ECG lead signals and (b) patient independent synthesized ECG lead signals.

22. A system according to claim 19, including,
a source of data representing accuracy values corresponding to sets of data representing patient specific synthesized ECG lead signals and patient independent synthesized ECG lead signals and wherein
said at least one display image shows accuracy values associated with said patient specific synthesized ECG lead signals and with said patient independent synthesized ECG lead signals.

23. A method supporting operation of an elecrtocardiogram (ECG) system, comprising the steps of:
storing a plurality of subsets of data representing ECG lead signals associated with a corresponding plurality of sets of ECG electrode configurations;
adaptively generating a set of synthesized data representing a selected one of, (a) patient specific synthesized ECG lead signals and (b) patient independent synthesized ECG lead signals, in response to user command, said synthesized data being generated using the plurality of subsets of data representing ECG lead signals; and
initiating generation of data representing at least one display image showing said synthesized data.

* * * * *